(12) United States Patent
Miles et al.

(10) Patent No.: US 6,787,018 B1
(45) Date of Patent: Sep. 7, 2004

(54) DIELECTROPHORETIC CONCENTRATION OF PARTICLES UNDER ELECTROKINETIC FLOW

(75) Inventors: Robin R. Miles, Danville, CA (US); Kerry A. Bettencourt, Dublin, CA (US); Christopher K. Fuller, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 300 days.

(21) Appl. No.: 09/733,857

(22) Filed: Dec. 8, 2000

(51) Int. Cl.⁷ .................... G01N 24/447; G01N 27/453
(52) U.S. Cl. ................. 204/643; 204/547; 204/450; 204/600; 204/601; 204/451
(58) Field of Search .................. 204/450, 466, 204/547, 600, 451, 601, 606, 616, 643

(56) References Cited

U.S. PATENT DOCUMENTS

| | | | |
|---|---|---|---|
| 4,326,934 A | 4/1982 | Pohl | 204/108 R |
| 5,344,535 A | 9/1994 | Betts et al. | 204/183.1 |
| 5,569,367 A | 10/1996 | Betts et al. | 204/547 |
| 6,287,832 B1 * | 9/2001 | Becker et al. | 435/173.9 |
| 6,296,752 B1 * | 10/2001 | McBride et al. | 204/547 |

OTHER PUBLICATIONS

Bakewell et al. ("Characterisation of the dielectrophoretic movement of DNA in micro–fabricated structures", Inst. Phys. Conf. Ser. No. 163, Mar. 1999, pp. 73–76).*

Morishima et al. ("Novel Separation Method on a Chip Using Capillary Electrophoresis in Combination with Dielectrophoresis", Micro. Total Analysis Systems 2000, May 14–18, 2000, pp. 269–272).*

S. Fiedler et al, Dielectrophoretic Sorting of particles and Cells in a Microsystem, Anal. Chem. 1998, 70, 1909–1915.

N.G. Green et al, Separation of submicrometre particles using a combination of dielectrophoretic and electrohydrodynamic forces, J. Phys. D., Appl. Phys. 31, (1998) L25–L30.

J. Suehiro et al, The dielectrophoretic movement and positioning of a biological cell using a three–dimensional grid electrode system, J. Phys D: Appl. Phys. 31 (1998) 3298–3305.

* cited by examiner

Primary Examiner—Alex Noguerola
(74) Attorney, Agent, or Firm—Eddie E. Scott; L. E. Carnahan; Alan H. Thompson

(57) ABSTRACT

The use of dielectrophoresis to collect particles under the conditions of electrokinetically-driven flow. Dielectrophortic concentration of particles under electrokinetic flow is accomplished by interdigitated electrodes patterned on an inner surface of a microfluid channel, a DC voltage is applied across the ends to the channel, and an AC voltage is applied across the electrodes, and particles swept down the channel electrokinetically are trapped within the field established by the electrodes. The particles can be released when the voltage to the electrodes is released.

6 Claims, 1 Drawing Sheet

DIELECTROPHORETIC CONCENTRATION OF PARTICLES UNDER ELECTROKINETIC FLOW

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to the concentration of particles in microfluidic devices, particularly to the use of dielectrophoresis to collect or concentrate the particles, and more particularly to the use of dielectrophoresis to collect particles under the conditions of electrokinetically-driven flow.

Microfluidic devices are most useful when operating with small sample volumes. Small sample volumes result in increased reaction times and reduced reagent use which means significantly reduced costs for the multitude of tests that one desires to conduct on any given sample. Dielectrophoretic concentration of the samples is a useful method for achieving these goals. Dielectrohporesis is attractive on the microfluidic scale because the forces become significant and useful at dimensions of less than 1 mm. Electrokinetic/electroosmotic flow is also useful in these devices because it obviates the need for micropumps and microvalves.

The present invention involves the combination of dielectrophoresis (DEP) and electrokinetic/electroosmotic flow. Such combination would not normally be an obvious choice since one might think that the two electric fields and their associated double charge layers may interfere with each other. Also, dielectrophoresis collection works best in the slow boundary-layer flow normally associated with pressure-driven flow. However, by the present invention, it has been found that particles can still collect even in the more uniform flow field associated with electroosmotic flow. The 5–10 mm double charge layer associated with establishing electroosmotic flow does not interfere, or be interfered with, by the DEP field in a significant way.

SUMMARY OF THE INVENTION

It is an object of the present invention to collect particles in a microfluidic channel using dielectrophoresis.

A further object of the invention is to provide for dielectriphoretic concentration of particles under electrokinetic flow.

Another object of the invention is to use delectrophoresis to collect particles under the conditions of electrokinetically-driven flow.

Another object of the invention is to use a combination of dielectrophoresis and electrokinetic/electroosmotic flow for the collection of particles in a microfluidic device.

Another object of the invention is to provide a microfluidic device capable on dielectrophoretic concentration of particles under electrokinetic flow.

Other objects and advantages of the present inventions will become apparent from the following description and accompanying drawing. Basically the present invention involves a method and apparatus for collecting or concentrating particles in a microfluidic channel using dielectrophoresis under conditions of electrokinetically-driven flow. This is accomplished by interdigitated electrodes patterned on the inner surface of a microfluidic channel, preferable formed of glass, applying a DC voltage across the ends of the channel to initiate an electrokinetic/electroosmotic flow field, and applying an AC voltage across the interdigitated electrodes to set up a non-uniform electric field capable of trapping particles using the dielectrophortic force. The trapped particles are released upon removal of the voltage to the electrodes.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

The present invention is directed to dielectrophoretic concentration of particles under electrokinetic flow. The present invention involves a method and apparatus for collecting particles in a microfluidic channel using the combination of dielectrophoresis and electrokinetic/electroosmotic flow. Electrokinetically-driven flow is an important technique for moving fluids and sample around a microfluidic bio-chemical assay chip, and the combination with the advantages of dielectrophoretic manipulation in this regime significantly advances this field of technology.

Figure 1:
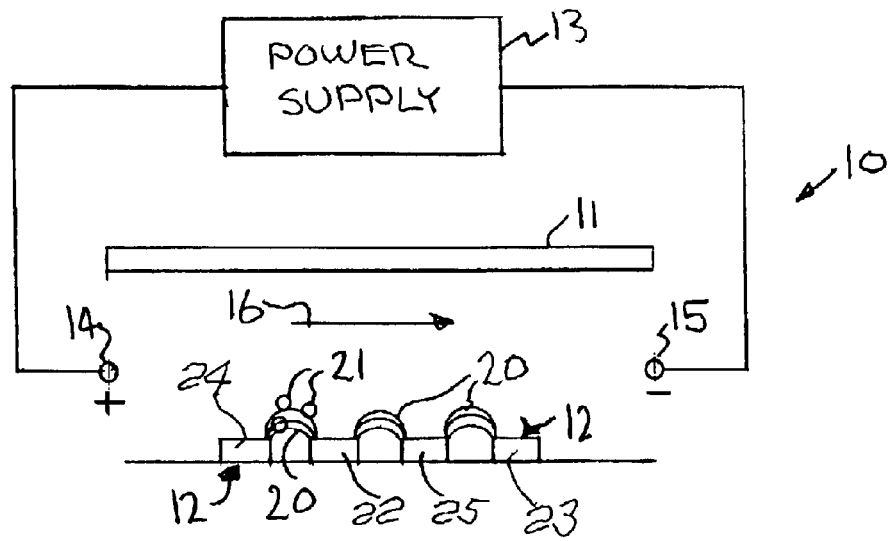
FIG. 1 is a schematic illustration of a microfluidic eletrokinetic flow channel with interdigitated electrodes located along the length of the channel.
Figure 2:
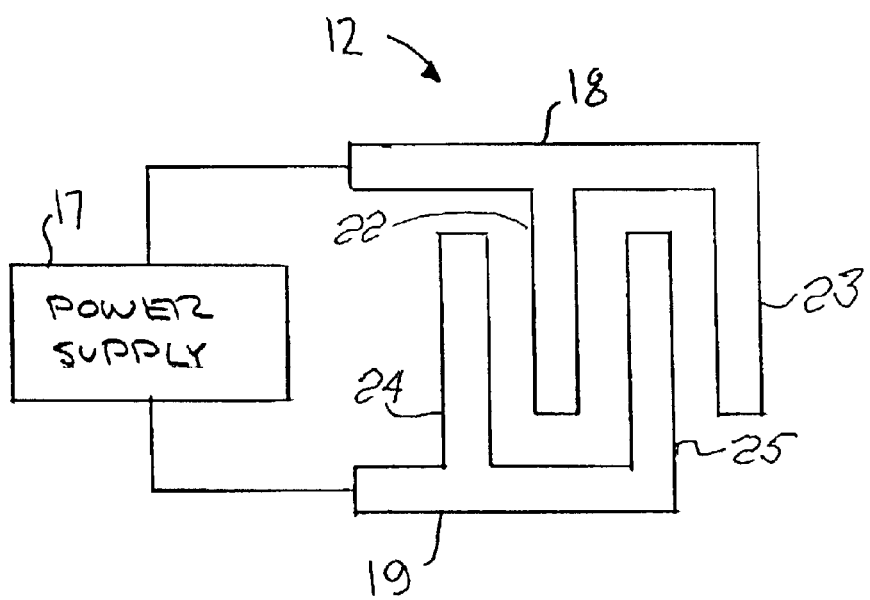
FIG. 2 is a greatly enlarged top view of the interdigitated electrodes of FIG. 1 and AC power source therefor.

FIGS. 1 and 2 schematically illustrate an embodiment of an apparatus for carrying out the present invention, with FIG. 2 being a top view of a pair of interdigitated electrodes of FIG. 1. Interdigitated electrodes are patterned on the inner surface of a microfluidic channel but can be suspended within the fluid. Glass is the preferred material for the microfluidic channel because it promotes electroosmotic flow, particularly if preconditioned with sodium hydroxide. However, other materials, such as certain types of plastics may be utilized. A direct current (DC) voltage is applied across the ends of the channel to initiate the electrokinetic/electroosmotic flow field. An alternating current (AC) voltage is applied across the interdigitated electrodes to set up a non-uniform electric field capable of trapping particles using the dielectrophoretic force. Particles are swept down the channel electrokinetically and are trapped within the field established by the interdigitated electrodes. The trapped particles can be released when the voltage to the interdigitated electrodes is released. Thus, this approach enables concentration of the sample prior to testing, since dielectrophoresis effects the motion on polarizable particles within a non-uniform electric field. Positive dielectrophoresis can be used to concentrate particles in areas of high electric field gradients, and can be used to eliminate the use of centrifuging to concentrate biological samples. Negative dielectrophoresis can be used to discriminate between various types of biological particles.

Referring now to the drawings, a microfluidic device generally indicated at 10 includes at least one microfluidic channel 11, having a pair of spaced sets of interdigitaled electrodes generally indicated at 12 patterned on the inner surface of the channel 11, which, for example, may be formed of bonded glass plates with the channel 11 formed therein as known in the art. A DC voltage supply 13 having a positive electrode 14 and a negative electrode 15 located at opposite ends of channel 11 produces a voltage across the ends of the channel 11 to initiate an electrokinetic/electroosmotic flow field indicated by arrow 16. An AC power supply 17 provides a voltage which is applied across the electrode plates 18 and 19 of interdigitated electrodes 12, as shown in FIG. 2, which set up a non-uniform electric field 20 capable of trapping particles 21 using the dielectriphoretic force. Each of electrode plates 18 and 19 include projecting legs 22–23 and 24–25, with leg 22 located intermediate legs 24 and 25 and with leg 25 been located intermediate legs 22 and 23.

It has thus been shown that the present invention provides for dielectrophoretic concentration of particles under electrokinetic flow, by using at least one set of interdigitated electrodes patterned on the inner surface of a microfluidic channel. Particles swept down the channel electrokinetically are trapped within the field established by the interdigitated electrodes. Thus, the apparatus can be used to concentrate the sample prior to testing due to the combined use of dielectrophoresis and electrokinetic/electroosmotic flow. While only one microfluidic channel has be shown, the present invention can be applied to microfluidic devices having a number of channels.

While a particular embodiment has been illustrated and described to exemplify and teach the principles of the invention, such is not intended to be limiting. Modifications and changes may become apparent to those skilled in the art, and it is intended that the invention be limited only by the scope of the appended claims.

What is claimed is:

1. An apparatus for dielectrophoretic concentration of particles under electrokinetic flow and collecting said particles in a microfluidic channel using a combination of dielectrophoresis and electrokinetic/electroosmotic flow, comprising:

a microfluidic channel section, said microfluidic channel section having a first end and a second end, means for producing electrokinetic flow in said microfluidic channel section by producing a DC voltage across said first end and said second end of said microfluidic channel section, said means for producing electrokinetic flow in said microfluidic channel section by producing a DC voltage across said first end and said second end of said microfluidic channel section comprising a positive electrode connected to said first end of said microfluidic channel section and a negative electrode connected to said second end of said microfluidic channel section and a DC power supply connected to said positive electrode and said negative electrode, at least one pair of interdigitated electrodes located on a surface of said microfluidic channel, said interdigitated electrodes comprising a first electrode plate having first electrode projecting legs and a second electrode plate having second electrode projecting legs, said first electrode projecting legs and said second electrode projecting legs interlaced, and means for producing said combination of dielectrophoresis and electrokinetic/electroosmotic flow by producing an AC voltage across the interdigitated electrodes, said means for producing said combination of dielectrophoresis and electrokinetic/electroosmotic flow comprising an AC power supply connected to said first electrode plate having first electrode projecting legs and said second electrode plate having second electrode projecting legs which sets up a non-uniform electric field proximate said first electrode plate having first electrode projecting legs and said second electrode plate having second electrode projecting legs, said non-uniform electric field collecting said particles.

2. The apparatus of claim 1, wherein said at least one pair of interdigitated electrodes located on a surface of said microfluidic channel comprises a plurality of pairs of interdigitated electrodes along a length of said microfluidic channel section.

3. In a microfluidic device using electrokinetic/electroosmotic flow to sweep particles down a microfluidic channel section for dielectrophoretic concentration of particles under and collecting said particles in said microfluidic channel section using a combination of dielectrophoresis and electrokinetic/electroosmotic flow, said microfluidic channel section having a first end, a second end and an inner section, an improvement comprising:

means for producing said electrokinetic/electroosmotic flow in said microfluidic channel section by producing a DC voltage across said first end and said second end of said microfluidic channel section, said means for producing said electrokinetic/electroosmotic flow in said microfluidic channel section by producing a DC voltage across said first end and said second end of said microfluidic channel section comprising a positive electrode connected to said first end of said microfluidic channel section and a negative electrode connected to said second end of said microfluidic channel section and a DC power supply connected to said positive electrode and said negative electrode, interdigitated electrodes patterned on said inner surface of said microfluidic channel section, said interdigitated electrodes comprising a first electrode plate having first electrode projecting legs and a second electrode plate having second electrode projecting legs, said first electrode projecting legs and said second electrode projecting legs interlaced, and means for producing said combination of dielectrophoresis and electrokinetic/electroosmotic flow by applying an AC voltage across said interdigitated electrodes to set up a non-uniform electric field capable of trapping said particles using a dielectrophoretic force as said particles are swept down the microfluidic channel electrokinetically said means for producing said combination of dielectrophoresis and electrokinetic/electroosmotic flow comprising an AC power supply connected to said first electrode plate having first electrode projecting legs and said second electrode plate having second electrode projecting legs which sets up said non-uniform electric field proximate said first electrode plate having first electrode projecting legs and said second electrode plate having second electrode projecting legs, said non-uniform electric field trapping said particles.

4. The improvement of claim 3, wherein said interdigitated electrodes patterned on said inner surface of said microfluidic channel section comprises a plurality of spaced pairs of interdigitated electrode located along a length of said microfluidic channel section.

5. The improvement of claim 3, wherein said patterned interdigitated electrodes each comprises a first section with spaced second and third sections extending transversely from said first section, said first section of each electrode being positioned substantially parallel, with a third section of one of the electrodes being located intermediate the spaced second and third sections of the other electrode.

6. A method for concentrating particles under flow, comprising:

forming at least one pair of interdigitated electrodes on a fluidic microchannel having a multiplicity of first electrode projecting legs and a second multiplicity of electrode electrode projecting legs, positioning at least one pair of interdigitated electrodes so that said first electrode projecting legs and said second electrode projecting legs are interlaced, and sweeping said particles through said fluidic microchannel by applying an AC voltage across the interdigitated electrodes to establish a non-uniform electric field capable of trapping particles using an dielectrophoretic force, controlling said voltage applied to each pair of interdigitated electrodes, and applying a DC voltage across ends of the fluidic microchannel to initiate an electrokinetic/electroosmotic flow field.

\* \* \* \* \*